United States Patent [19]

Milzner et al.

[11] Patent Number: 4,657,579

[45] Date of Patent: Apr. 14, 1987

[54] NOVEL N-(5-PYRIMIDINYL)-CHLOROACETAMIDES

[75] Inventors: Karlheinz Milzner, Basel, Switzerland; Fred Kuhnen, Weil; Karl Seckinger, Riegel, both of Fed. Rep. of Germany

[73] Assignee: Sandoz Ltd., Basel, Switzerland

[21] Appl. No.: 708,694

[22] Filed: Mar. 6, 1985

Related U.S. Application Data

[63] Continuation of Ser. No. 529,400, Sep. 6, 1983, abandoned.

[30] Foreign Application Priority Data

Sep. 13, 1982 [GB] United Kingdom ................ 8226004
Sep. 1, 1983 [CH] Switzerland ..................... 04800/83
Feb. 22, 1985 [GB] United Kingdom ................ 8504609

[51] Int. Cl.⁴ .............. C07D 239/42; C07D 239/47; A01N 43/54

[52] U.S. Cl. ............................... 71/92; 71/90; 544/296; 544/319; 544/322; 544/326; 544/328

[58] Field of Search .............. 544/322, 319, 326, 328, 544/296; 71/92, 90

[56] References Cited

FOREIGN PATENT DOCUMENTS

3331873  3/1984  Fed. Rep. of Germany ...... 544/322
1583150 10/1979  France ........................... 544/322

OTHER PUBLICATIONS

Bell et al, J. Org. Chem. 26 3534 (1961).

*Primary Examiner*—Robert Gerstl
*Attorney, Agent, or Firm*—Gerald D. Sharkin; Richard E. Vila

[57] ABSTRACT

The invention provides novel pyrimidine compounds substituted in the 5-position by a chloroacetylamino group which are useful as herbicides. Other objects of the invention are herbicidal compositions comprising such novel compounds and methods of combatting weeds with the aid of said novel compounds.

19 Claims, No Drawings

NOVEL N-(5-PYRIMIDINYL)-CHLOROACETAMIDES

This application is a continuation in part of Application Ser. No. 529,400 filed Sept. 6, 1983, now abandoned.

The present invention relates to pyrimidine compounds substituted in the 5-position by a chloroacetylamino group, their use as herbicides, agricultural compositions for facilitating such use and the preparation of the novel compounds of the invention.

The present invention provides compounds of formla I

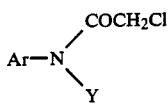    I wherein
Ar is 5-pyrimidinyl unsubstituted or substituted and
Y is a hydrocarbon selected from $C_{1-8}$alkyl, $C_{3-8}$alkenyl, $C_{3-8}$alkinyl, $C_{3-8}$cycloalkyl, $C_{5-8}$cycloalkenyl, $C_{3-8}$cycloalkyl-$C_{1-5}$alkyl, whereby such hydrocarbon is unsubstituted or substituted by halogen selected from F, Cl or Br;
or is a group $CH(R_1)$-$COY_1$,
wherein
$R_1$ is H or $C_{1-5}$alkyl and
$Y_1$ forms together with the CO-group to which it is bound an ester or amide function;
or is a group $R_2$-$A_z$,
wherein
$R_2$ is $CH_2$ or $CH_2$-$CH_2$ unsubstituted or substituted by $C_{1-5}$alkyl and
$A_z$ is a di- or triazole linked by one of its nitrogen atoms to $R_2$, or is a 5-membered aromatic heteroring linked by a C-atom of said ring to $R_2$ and having 1, 2 or 3 heteroatoms selected from the group consisting of O, S or N, or is a pyrimidinyl group or is a group A-O-$R_3$,
wherein
$R_3$ is H, or is a hydrocarbon selected from the group consisting of $C_{1-8}$alkyl, $C_{3-8}$alkenyl, $C_{3-8}$alkinyl, $C_{3-8}$cycloalkyl, $C_{5-8}$cycloalkenyl or $C_{3-8}$cycloalkyl-$C_{1-5}$alkyl, which is unsubstituted or substituted, or is phenyl; or is

wherein
$R_4$ is hydrocarbon selected from $C_{1-5}$alkyl, $C_{3-5}$alkenyl, $C_{3-5}$alkinyl, $C_{3-8}$cycloalkyl, $C_{5-8}$cycloalkenyl, $C_{3-8}$cycloalkyl-$C_{1-5}$alkyl, whereby the hydrocarbon is unsubstituted or substituted by halogen selected from F, Cl or Br; or is allene
$R_4'$ is H or has one of the meanings defined for $R_4$ and
A is a hydrocarbon moiety, which may be linked with $R_3$ to form a saturated oxygen containing heterocyclic ring comprising 1 or 2 oxygens as heteroatom, and whereby the N and O atoms to which it is bound are separated by up to 3 C-atoms;

or is a group

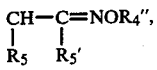

wherein
$R_4''$ has one of the significances defined for $R_4$
$R_5$ and $R_5'$ are independently H or $CH_3$ or
$R_5$ together with $R_5'$ are $(CH_2)_3$ or $(CH_2)_4$
or is allene or $CH_2$—$CH$=$C$=$CH_2$
or is a group

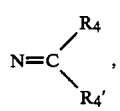

wherein $R_6$ is H or $C_{1-3}$alkyl and B is a group selected from $N(CH_3)COCH_3$, or a 5-membered lactam linked with its N-atom to the $CHR_6$ group, in free base form or in acid addition salt form.

The Ar group may be unsubstituted or substituted. Where Ar is substituted it may bear substituents in any possible position; preferred positions of such substituents are in o- or o'-position of the chloroacetamide group, whereby additional substituents may be present. Especially preferred Ar significances are 4,6-disubstituted 5-pyrimidinyl groups (unsubstituted in the 2-position). Examples of suitable substituents of Ar are halogen selected from F, Cl and Br; $C_{1-4}$alkyl e.g. $CH_3$ and $C_2H_5$ unsubstituted or substituted, for example, by $C_{1-4}$alkoxy (e.g. $CH_3O$, $C_2H_5O$) or by halogen (e.g. F, Cl, Br); formyl and acetals [e.g. $CH(OC_{1-2}alkyl)_2$] or oximes (e.g. $CH$=$NOCH_3$) thereof; $C_{2-4}$alkanoyl (e.g. $COCH_3$) and ketals or oximes thereof; an ether or thioether group (e.g. $C_{1-8}$alkoxy, benzyloxy, phenoxy, di($C_{1-4}$alkyl)amino-$C_{1-4}$alkylene-oxy, $C_{1-4}$alkoxy-$C_{1-4}$alkylene-oxy, $C_{1-4}$alkylthio-$C_{1-4}$alkylene-oxy, $C_{1-8}$alkylthio); an amino group (e.g. di-$C_{1-4}$alkylamino, N-$C_{1-4}$alkyl-N-phenylamino). A particularly suitable sub-group of Ar significances are 5-pyrimidinyl groups substituted in 4- and/or 6-position by at least one substituent and preferably both substituents selected from the group consisting of $C_{1-4}$alkoxy, di($C_{1-4}$alkyl)amino, $C_{1-4}$alkylthio and $C_{1-4}$alkyl. A preferred sub-group of Ar significances are 5-pyrimidinyl groups bearing in the 4-position an $C_{1-4}$alkoxy or a di($C_{1-4}$alkyl)amino group and in the 6-position a substituent selected from the group consisting of $C_{1-4}$alkoxy, di($C_{1-4}$alkyl)amino, $C_{1-4}$alkyl or $C_{1-4}$alkylthio, more preferably a substituent selected from the group consisting of $C_{1-4}$alkoxy, di($C_{1-4}$alkyl)amino or $C_{1-4}$alkyl. In a particularly preferred sub-group of Ar significances, the 5-pyrimidinyl group is substituted in the 4- and 6-position by a substituent selected from the group consisting of $C_{1-4}$alkoxy and di($C_{1-4}$alkyl)amino, e.g. 4-$C_{1-4}$alkoxy-5-pyrimidinyl substituted in the 6-position by $C_{1-4}$alkoxy or di($C_{1-4}$alkyl)amino. In another particularly preferred subgroup of Ar significances, the 5-pyrimidinyl group is substituted in the 4-position by a N,N-di($C_{1-4}$alkyl)amino group (such as dimethylamino, diethylamino, N-n-butyl-N-methylamino) or 1-pyrrolidinyl and in the 6-position by a group selected from Cl; O-($C_{1-8}$alkyl) such as methoxy, ethoxy, propoxy(n- or iso-), butoxy(n- or iso-, sec- or tert-), pentoxy (e.g. n-pentoxy; 2,2-dimethylpropoxy or 2-pentoxy), hexyloxy (e.g. n-hexyloxy), heptyloxy (e.g. 2-ethyl-2-methyl-butoxy); O-$C_{3-5}$alkenyl or O-$C_{3-5}$alkinyl such as O-$CH_2$-CH=$CH_2$, O—$CH_2$-C($CH_3$)=$CH_2$ or O-$CH_2$-C≡CH; or S-$C_{1-8}$alkyl such as S-$CH_3$.

Very suitable $C_{1-8}$alkoxy substituents of the 5-pyrimidinyl group are i.a. $C_{1-3}$alkoxy substituents, particularly $CH_3O$, $C_2H_5O$ and i—$C_3H_7O$.

Very suitable di($C_{1-4}$alkylamino) substituents of the 5-pyrimidinyl group are i.a. di($C_{1-3}$alkyl)amino, more preferably di($C_{1-2}$alkyl)amino, particularly N($CH_3$)$_2$.

Very suitable $C_{1-8}$alkylthio substituents of the 5-pyrimidinyl group have 1–4, more preferably 1–3, particularly 1 C-atom.

Very suitable $C_{1-4}$alkyl substituents of the 5-pyrimidinyl group have 1–3, preferably 1–2, particularly 1 C-atom.

Particular subsubstituents of interest for the 2-, 4- and 6-positions of the 5-pyrimidinyl group are those independently selected from the group consisting of H; F; Cl; Br; $C_{1-4}$alkyl optionally substituted by F, Cl, Br or $C_{1-4}$alkoxy; formyl; CH=$NOCH_3$; $C_{2-4}$alkanoyl; CH(O$C_{1-2}$alkyl)$_2$; $C_{1-8}$alkylthio; $C_{1-8}$alkoxy; benzyloxy; phenoxy, di($C_{1-4}$alkyl)amino-$C_{1-4}$alkylenoxy; $C_{1-4}$alkoxy-$C_{1-4}$alkyleneoxy; $C_{1-4}$alkylthio-$C_{1-4}$alkylenoxy; di-$C_{1-4}$alkylamino; N-$C_{1-4}$alkyl-N-phenylamino; and 1-pyrrolidinyl.

Where Y, $R_4$ and $R_4'$ are hydrocarbon substituted by halogen, such halogen is preferably Cl or Br.

Where Y, $R_3$, $R_4$ and/or $R_4'$ are $C_{1-8}$alkyl, $C_{3-8}$alkenyl or $C_{3-8}$alkinyl, they preferably have up to 5 C-atoms. Where Y, $R_3$, $R_4$ and/or $R_4'$ are or contain cycloalkyl or cycloalkenyl such cyclic hydrocarbon groups contain preferably up to 6 C-atoms.

Where $R_1$ is $C_{1-5}$alkyl it is preferably $CH_3$ or $C_2H_5$, particularly $CH_3$. The term ester or amide function used in connection with the meaning of $Y_1$ is intended to embrace any function which can be regarded as theoretically obtainable by the reaction of the COOH group of an acid with any organic, proton supplying compound reacting with such acid with the elimination of water e.g. an alcohol, an amine, a mercaptan, an oxime, a hydrazine, hydrazide or hydrazone (whereby the term "theoretically obtainable" indicates the fact—generally known to those skilled in the art—that in practise such reaction will be effected by activating the OH group of the carboxylic acid, the eliminated compound being then the reaction product of the activated group with the proton of the organic, proton supplying compound).

An example of a suitable $Y_1$ significance is e.g. $C_{1-4}$alkoxy.

Where $R_2$ is $CH_2$ it may be substituted by 1 or 2, preferably 1 $C_{1-5}$alkyl. Where $R_2$ is $CH_2CH_2$ it may be substituted by up to 4 $C_{1-5}$alkyl group and is preferably mono- or disubstituted. Where $CH_2CH_2$ is disubstituted, the substituents are preferably at different C-atoms.

Preferred $C_{1-5}$alkyl substituents of $R_2$ are $CH_3$ and $C_2H_5$, particularly $CH_3$.

Where $A_z$ is di- or triazole it is preferably 1-pyrazolyl, 1-imidazolyl, 1,2,3-triazol-1-yl or 1,2,4-triazol-1-yl, particularly 1-pyrazolyl.

Where $A_z$ is the above defined 5-membered aromatic heteroring, such ring is e.g. a thienyl, a 1,3-thiazolyl, a 1,2-thiazolyl, an 1,2- or 1,3-oxazolyl, an 1,2,4- or 1,3,4-oxadiazolyl or a 1,2,5-thiadiazolyl group.

Where $A_z$ is pyrimidinyl, such ring may be linked by its 2-, 4- or 5-C-atom to $R_2$, but preferably by its 2-C-atom (i.e. 2-pyrimidinyl).

$A_z$ may be unsubstituted or substituted.

Suitable substituents of $A_z$ are e.g. one or more $C_{1-5}$alkyl groups, such as $CH_3$.

Where $R_3$ is the above defined hydrocarbon, such hydrocarbon may be unsubstituted or substituted, e.g. by halogen, an azole group such as 1-pyrazolyl and/or by alkoxy, preferably by $C_{1-4}$alkoxy such as $CH_3O$. Examples of particularly suitable $R_3$ significances are $CH_3$, $C_2H_5$, $CH_2CH=CH_2$, $CH_2C≡CH$ and $(CH_2)_2OCH_3$.

Suitable meanings of A-O-$R_3$, when A is linked with $R_3$ to form a ring, are e.g. 1,3-dioxolane-4-ylmethyl, 1,3-dioxolane-4-yl-ethyl and 1,3-dioxolane-2-ylmethyl.

Where A is not linked with $R_3$ to form a ring, A is $C_{1-8}$alkylene, separating the O- and N-atom to which it is bound by 1 to 3, preferably 1 or 2 C-atoms. Examples of suitable A significances are $CH_2$ and $(CH_2)_2$.

A may be unsubstituted or substitted, e.g. by $C_{1-5}$alkoxy (such as $OCH_3$).

$R_4$, $R_4'$ and $R_4'$ are preferably $C_{1-4}$alkyl.

$R_5$ and $R_5'$ are preferably H or $CH_3$.

The term lactam as used in connection with the meaning of B includes any 5-membered saturated N-containing heteroring, linked with its N-atom to the $CHR_6$ group and having in ortho-position of said N-atom a carbonyl function, said heteroring containing optionally an additional heteroatom (O, S, N), an additional carbonyl function and/or $C_{1-5}$alkyl substituents, or being optionally fused to a benzene ring, which may be substituted e.g. by halogen. A suitable example of such bicyclic lactam is 2-oxo-1,3-benzthiazol-3-yl.

A preferred sub-group of the compound of the invention are those of the formula I':

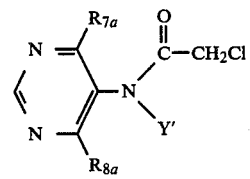

wherein
$R_{7a}$ and $R_{8a}$ are independently F, Cl, Br, $C_{1-4}$alkyl, $C_{1-8}$alkoxy, $C_{3-5}$alkenyloxy, $C_{3-5}$alkinyloxy, $C_{1-8}$alkylthio, di($C_{1-4}$alkyl)amino or 1-pyrrolidinyl,
and Y' is
(a') a hydrocarbon selected from the group consisting of $C_{3-5}$alkenyl and $C_{3-5}$alkinyl, which hydrocarbon is optionally mono-substituted by F, Cl or Br;
(b') $C_{1-3}$alkoxy-$C_{1-3}$alkylene optionally mono-substituted by $C_{1-4}$alkoxy;
(c') $C_{3-5}$alkinoxy-$C_{1-3}$alkylene;
(d') $C_{3-5}$alkenoxy-$C_{1-3}$alkylene;
(e') $CH_2$-CH=CH=$CH_2$;
(f') CH($R_6'$)$A_z'$
  wherein
  $R_6'$ is H or $CH_3$ and
  $A_z'$ is
    (i) 1-pyrazolyl, 3,5-dimethyl-1-pyrazolyl, 1-imidazolyl, 1,2,3-triazol-1-yl or 1,2,4-triazole-1-yl;
    (ii) a 5-membered aromatic heteroring linked by a C-atom thereof to the CH($R_6'$) group of CH($R_6'$)$A_z'$ and having 1 to 3 heteroatoms selected from the group consisting of O, S and N; or (iii) 2-pyrimidinyl; such $A_z'$ heteroring being optionally mono- or di-substituted on a ring C-atom thereof by $C_{1-4}$alkyl;

(g') $CHR_5—CHR_5'=NO(C_{1-4}alkyl)$;

(h') $CH(R_6)B'$
  wherein B' is
  (i) $N(CH_3)COCH_3$; or
  (ii) 2-oxo-3-benzthiazolidinyl optionally mono-substituted by F, Cl or Br;

or (i') $CH(R_6)COY_1'$ in which $Y_1'$ is di($C_{1-4}$alkyl)amino or $C_{1-4}$alkoxy, and $R_5$, $R_5'$ and $R_6$ are as above defined.

Another preferred sub-group of compounds of the invention are compounds of formula Ia

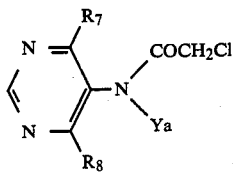

wherein $R_7$ and $R_8$, independently, are $C_{1-4}$alkyl, $C_{1-4}$alkoxy $C_{1-4}$alkylthio or di($C_{1-4}$alkyl)amino, and Ya is $C_{3-5}$alkenyl or $C_{3-5}$alkinyl unsubstituted or mono-substituted by halogen selected from F, Cl, Br or is $C_{1-3}$alkoxy-$C_{1-3}$alkylene unsubstituted or mono substituted by $C_{1-4}$alkoxy; or is $C_{3-5}$alkinoxy-$C_{1-3}$alkylene; or is $C_{3-5}$alkenoxy-$C_{1-3}$alkylene; or is $CH_2-CH=C=CH_2$; or is $CH_2A_z'$, $CHR_5—CHR_5'=NO(C_{1-4}alkyl)$, $CH(R_6)B'$ or $CH(R_6)COY_1'$, wherein $A_z'$ is a heteroring selected from 1-diazolyl, 1-triazolyl, a 5-membered aromatic heteroring linked by a C-atom of said ring to the $CH_2$ group and having 1 to 3 heteroatoms selected from the group consisting of O, S or N, and 2-pyrimidinyl whereby the heteroring may be unsubstituted or substituted by 1 or 2 groups selected from $C_{1-4}$alkyl, halogen (e.g. Cl), $C_{1-4}$alkoxy (e.g. $OCH_3$), $C_{1-4}$alkylthio (e.g. $SCH_3$), and di($C_{1-4}$alkylamino), (e.g. $N(CH_3)_2$)

B' is $N(CH_3)COCH_3$; 2-oxo-3-benzthiazolidinyl unsubstituted or mono-substituted by halogen selected from F, Cl and Br, $Y_1'$ is di($C_{1-4}$alkyl)amino or $C_{1-4}$alkoxy, and $R_5$, $R_5'$ and $R_6$ are as defined above.

In a preferred sub-group of compounds of formula Ia, one of $R_7$ and $R_8$ is selected from the group consisting of $C_{1-4}$alkoxy and di($C_{1-4}$alkyl)amino. Particularly suitable $C_{1-4}$alkoxy significances of $R_7$ and $R_8$ are e.g. $CH_3O$, $C_2H_5O$, i-$C_3H_7O$ and n-$C_4H_9O$, especially i-$C_3H_7O$.

A particularly suitable di($C_{1-4}$alkyl)amino significance of $R_7$ and $R_8$ is i.a. $N(CH_3)_2$.

Where any of $R_7$ and $R_8$ is $C_{1-4}$alkyl or $C_{1-4}$alkylthio it is preferably $CH_3$ or $CH_3S$ resp.

Examples of very suitable A'z significances are 1,2,4-triazol-1-yl, 2-methyl-1,3,4-oxadiazol-5-yl, 3-methyl-1,2,4-oxadiazol-5-yl, 3-methyl-isoxazol-5-yl, 2-methyl-thiazol-4-yl, 2-thienyl, 2-pyrimidinyl and 1-pyrazolyl, particularly the latter.

Another preferred subgroup or compounds of the invention are compounds of formula Iaa

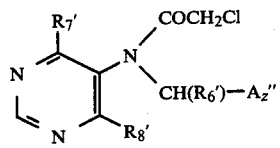

wherein $R_7'$ is a N,N-disubstituted amino group, $R_8'$ is halogen, $C_{1-4}$alkyl, or an ether or thio ether group, $A_z''$ is 1-pyrazolyl or 3,5-dimethyl-1-pyrazolyl and $R_6'$ is H or $CH_3$.

The present invention also provides a process for protecting a compound of formula I comprising (a) substituting in a compound of formula II

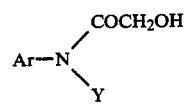

wherein Ar and Y are as defined above, the HO group of the N-hydroxyacetyl group by Cl, (b) N-alkylating a compound of formula III

wherein Ar is as defined above, with a compound of formula IV $$LY \qquad \qquad IV$$

wherein Y is as defined above, and L is a leaving group capable of being split off under the N-alkylation reaction conditions, (c) N-acylating a compound of formula V

wherein Ar and Y are as defined above, with chloroacetyl chloride.

Process (a) of the invention can be carried out by conventional manner under conditions known for the substitution of an OH group by a Cl.

Such substitution can for example be effected by treating a compound of formula II with a chlorinating agent, such as thionyl chloride under conditions known per se for analogous reactions.

According to a variante of this chlorination process, the compounds of formula II are first converted into the corresponding sulphonyloxy derivatives, e.g. by O-sulphonation with the aid of a sulphonyl halide, and such sulphonyloxy derivatives then converted into the desired compounds of formula I by nucleophilic substitution of the sulphonyloxy group by chlorine.

Reactants supplying the Cl anions required for such nucleophilic substitution are e.g. alkalimetal chlorides such as NaCl, quaternary tetrabutylammonium chloride or 4-dimethylaminopyridinehydrochloride. Such substitution is conveniently carried out in $CH_2Cl_2$ or in an aqueous/organic two-phase system, wherein the organic phase is e.g. a hydrocarbon such as toluene, in the presence of a suitable phase transfer catalyst, preferably with heating e.g. at 40° to 120° C.

Process (b) may be carried out by conventional manner under conditions known for the N-alkylation of amides. The reaction is advantageously carried out in a solvent which is inert under the reaction conditions e.g. dimethoxyethane or acetonitrile or in an aqueous/organic two-phase system in the presence of a phase transfer catalyst.

Suitable meanings of L (in formula IV) are Cl, Br or the sulphonyloxy moiety of an organic sulphonic acid such as mesyloxy or p-tosyloxy.

The compounds of formula III are preferably used in salt form, more preferably in alkalimetal salt form, e.g. the sodium salt form Such salts are obtained in conventional manner by reaction of the compound of formula III with a base such as an alkalimetal amide, hydride, hydroxide or alcoholate.

Process (c) may be carried out under the conditions known for the N-chloroacetylation of amines. Such reaction is conveniently carried out in the presence of an acid binding agent such as $K_2CO_3$.

The compounds of formula I may be recovered from the reaction mixture in which it is formed by working up by established procedures. They are obtained in free base form or in acid addition salt form. Free base forms of compounds of formula I may be converted into acid addition salt forms in conventional manner and vice versa.

The compounds of formulae II, III and V are novel. They may be prepared in conventional manner, e.g. starting from the corresponding 5-aminopyrimidines of formula VI

  Ar-NH$_2$    VI wherein Ar is as defined above.

The compounds of formula II may be obtained by reaction of a compound of formula VI with acetoxyacetyl chloride and subsequent hydrolysis of the so obtained acetoxyacetamide.

The compounds of formula III may be obtained by reaction of a compound of formula VI with chloroacetyl chloride.

The compounds of formula V may be obtained by N-alkylation of a compound of formula VI. Such alkylation can be carried out in conventional manner either directly, with the corresponding alkylating agents, or, where appropriate, reductively via the Schiff base or amide.

Several compounds of formula VI are known.

The novel compounds of formula VI may be obtained analogous to known processes. For example, 5-amino-4,6-dimethylpyrimidine, which is novel, may be obtained by catalytic hydrogenation of [4,6-dimethyl-2-thiopyrimidine-5-ylazo]benzene in the presence of Raney-Ni, as illustrated in the experimental part of this specification.

Many other novel compounds of formula VI may be obtained starting from 2,4-diHO-6-CH$_3$-pyrimidine or 4,6-dihydroxypyrimidine with the aid of various reaction methods in the appropriate order, examples of such reation methods being nitration (introduction of NO$_2$ with e.g. HNO$_3$)
chlorination (substitution of OH by Cl with the aid of e.g. OPCl$_3$)
alkoxylation (substitution of Cl by alkoxy with the aid of an alkalimetalalcoholate)
hydrogenation (reduction of NO$_2$ to NH$_2$ with H$_2$ in the presence of PdC)
amination (substitution of Cl by an amino group)
Cl elimination (by hydrogenation in the presence of PdC)

Insofar as the production of starting material is not described herein, these compounds are known, or may be produced and purified in accordance with known processes or in a manner analogous to processes described herein or to known processes.

The compounds of formula I are useful because they control or modify the growth of plants. By plants it is meant germinant seeds, emerging seedlings and established vegetation including underground portions.

In particular, the compounds are useful as herbicides as indicated by i.a. the damage caused to both monocotyledoneous and dicotyledoneous weeds such as *Lepidium sativum, Avena sativa, Agrostis alba* and *Lolium perenne* in tests by test dosages equivalent to an application rate of from 1.4 to 5.6 kg/ha after pre- or post-emergence application. In view of their herbicidal effect the compounds of the invention are indicated for use in combatting dicotyledoneous and grassy weeds, as confirmed by further evaluation with representative compounds with test dosages equivalent to an application rate of from 0.2 to 5.0 kg active ingredient, e.g. test dosages equivalent to a rate of 0.2, 1.0 and 5.0 kg active ingredient/ha, in dicotyledonous weeds such as *Amaranthus retroflexus, Capsella bursa-pastoris, Chenopodium album, Stellaria media, Senecio vulgaris* and *Galium aparine*, and, grassy weeds such as *Agropyron repens, Agrostis alba, Alopecurus myosuroides, Apera spica-venti, Avena fatua, Echinochloa crus-galli Setaria italica, Poa annua, Panicum miliaceum, Eleusin indica, Diguitaria sanguinalis* and *Sorghum halepense*.

The compounds of the invention are relatively less toxic towards crops, e.g. against grassy crops such as a small grain (winter cereals, rice) or corn and particularly against broad leaved crops such as cotton, sugar beet, potato, sunflower, rape or flax, than towards weeds. The compounds of the invention are therefore also indicated for use as selective herbicides in a crop locus.

The compounds of the invention have also an appropriate persistent activity which is essential for their practical use, and surprising in view of experiences with i.a. the compounds of the U.S. Pat. No. 4,282,028.

Many of the compounds of formula I, particularly such belonging to the subgroup of formula Iaa, in free base form or in agriculturally acceptable acid addition salt form, are useful in combatting perennial weeds.

Examples of perennial weeds that may be combatted with the compounds of formula I (in free base form or agriculturally acceptable salt form) are *Agropyron repens, Cynodon dactylon, Cyperus esculentus, Cyperus rotundus* and *Sorghum halepense* as established by tests on various perennial weeds with representative examples of the compounds of formula I with test dosages equivalent to an application rate of from 3 to 24 kg active ingredient/ha, e.g. a selection of test dosages equivalent to a rate of 3 kg, 6 kg and 12 kg or 8 kg, 16 kg and 24 kg/ha.

For use in combatting perennial weeds, the compounds of formula I may be applied pre-emergence or post-emergence to the weeds. In general post-emergence treatment will require rather higher application rates than pre-emergence treatment; on the other hand post-emergence application will allow a more rational treatment. In appropriate application rates, the compounds of formula I in free base or agriculturally acceptable acid addition salt form suppress the formation of new tubers, respectively may suppress the regrowth of perennial weeds cut after treatment.

Accordingly, the present invention provides a method of combatting weeds in a locus, preferably in a crop locus as mentioned above, which comprises applying to the locus a herbicidally effective amount of a compound of the invention (in free base form or agriculturally acceptable salt form). A particularly preferred and advantageous embodiment of the invention is the pre-emergence (both crops and weeds) use of a compound of formula I in selectively combatting weeds in a crop locus.

Another particularly preferred embodiment of the invention is the use of a compound of formula I, in free base form or in agriculturally acceptable acid addition salt form, in combatting perennial weeds comprising applying to the perennial weeds or the locus thereof a herbicidally effective amount of such compound.

Examples of suitable agriculturally acceptable acid addition salt forms of compounds of formula I are e.g. a hydrochloride or an acetate.

For general herbicidal as well as for selective herbicidal use of compounds of the invention, the amount to be applied to attain the desired effect will vary depending on the particular crop if employed for selective use and other standard variables such as the compound employed, mode of application, conditions of treatment, the target weeds and the like. The appropriate application rates can be determined by routine procedures by those skilled in the art, or by comparing the activity of the compounds of the invention with standards for which the application rate is known, e.g. in greenhouse tests. However, in general, satisfactory results against annual weeds are usually obtained when the compounds of the invention (in free base form or agriculturally acceptable acid addition salt form) is applied at a rate in the range of from about 0.1 to 5 kg/ha, preferably from about 0.2 to 4 kg/ha, more preferably from 0.5 to 3.0 kg/ha, the application being repeated as necessary. When used in a crop locus, the application rate should preferably not exceed 3 kg/ha. When applied pre-emergence, the particularly preferred application rate lies between 0.5 to 1.5 kg a.i./ha; when applied early post-emergence such particularly preferred application rate lies between 1.0 and 3.0 kg a.i./ha. When used in combatting perennial weeds, satisfactory results are usually obtained with an application rate in the range of from 1 to 18 kg/ha, preferably from 3 to 12 kg/ha.

Particularly suitable for use in combatting perennial weeds are compounds of formula Iaa, in free base form or in agriculturally acid addition salt form, especially such having one or more of the following features:

$R_7'$ is N,N-di($C_{1-4}$alkyl)amino such as $N(CH_3)_2$, $N(C_2H_5)_2$, $N(CH_3)n-C_4H_9$ or 1-pyrrolidinyl, $R_8'$ is Cl; O-($C_{1-8}$alkyl) such as methoxy, ethoxy, propoxy (n- or iso-), butoxy (n-, iso-, sec- or tert.), pentoxy (e.g. n-pentoxy, 2,2-dimethyl-propyl or 2-pentoxy), hexyloxy (e.g. n-hexyloxy), heptyloxy (e.g. 2-ethyl-2-methyl-butoxy); O-$C_{3-5}$alkenyl or O-$C_{3-5}$alkinyl such as O-$CH_2$-CH=$CH_2$, O-$CH_2$-C($CH_3$)=$CH_2$ or O-$CH_2$-C≡CH; or S-$C_{1-8}$alkyl such as S-$CH_3$;

$R_6'$ is H;

$R_7'$ is preferaby $N(CH_3)_2$, $N(C_2H_5)_2$ or 1-pyrrolidinyl, particularly $N(CH_3)_2$.

$R_8'$ is preferably Cl, O-($C_{1-4}$alkyl) or S-($C_{1-4}$alkyl). Other preferred significances of $R_8'$ are O-$CH_2$-CH=$CH_2$, O-$CH_2$-C($CH_3$)=$CH_2$ or O-$CH_2$-C≡CH.

The compounds of formula I in free base form or in agriculturally acceptable salt form may be and preferably are employed as herbicidal compositions in association with herbicidally acceptable diluent(s). Suitable formulations containing 0.01% to 99% by weight of active ingredient, from 0 to 20% herbicidally acceptable surfacent and 1 to 99.99% solid or liquid diluent(s). Higher ratios of surfactant to active ingredient are sometimes desirable and are achieved by incorporation into the formulation or by tank mixing. Application forms of composition generally contain between 0.01 and 25% by weight of active ingredient. Lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful formulations of the compounds of the invention include dusts, granules, pellets, suspension concentrates, wettable powders, emulsifiable concentrates and the like. They are obtained by conventional manner, e.g. by mixing the compounds of the invention with the diluent(s). More specifically liquid compositions are obtained by mixing the ingredients, fine solid compositions by blending and, usually grinding, suspensions by wet milling and granules and pellets by spraying the active material onto preformed granular carriers or by agglomeration techniques.

Alternatively, the compounds of the invention may be used in microencapsulated form.

Herbicidally acceptable additives may be employed in the herbicidal compositions to improve the performance of the active ingredient and to reduce foaming, caking and corrosion.

Surfactant as used herein means a herbicidally acceptable material which imparts emulsifiability, spreading, wetting, dispersibility or other surface-modifying properties. Examples of surfactants are sodium lignin sulphonate and lauryl sulphate.

Diluents as used herein mean a liquid or solid herbicidally acceptable material used to dilute a concentrated material to a usable or desirable strength. For dusts or granules it can be e.g. talc, kaolin or diatomaceous earth, for liquid concentrate forms, for example a hydrocarbon such as xylene or an alcohol such as isopropanol, and for liquid application forms i.a. water or diesel oil.

The compositions of this invention can also comprise other compounds having biological activity, e.g. compounds having similar or complementary herbicidal activity or compounds having antidotal, fungicidal or insecticidal activity.

Specific Examples of herbicidal compositions will now be described.

EXAMPLE A

Wettable Powder

25 Parts of a compound of formula I, e.g. the compound of Example 3 hereinafter given, are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE B

Emulsion Concentrate

25 Parts of a compound of formula I, e.g. the compound of Example 3 hereinafter given, 50 parts of xylene, 15 parts of dimethylformamide, and 10 parts of emulsifier (e.g. ATLOX 4851 B a blend of Ca alkylarylsulphonate and a polyethoxylated triglyceride of Atlas Chemie GmbH) are thoroughly mixed until a homogeneous solution is obtained. The resulting emulsion concentrate is diluted with water before use.

EXAMPLE C

Granules

5 Kg of a compound of formula I, e.g the compound of Example 3 hereinafter given, are dissolved in 15 l methylene chloride. The solution is then added to 95 kg of granulated attapulgite (mesh size 24/28 mesh/inch) and thoroughly mixed. The solvent is then evaporated off under reduced pressure.

The invention is further illustrated by the following Examples wherein temperatures are in °C.

FINAL COMPOUNDS

Example 1

(process a)

N-Propargyl-N-(4,6-dimethyl--2-dimethylaminopyrimidin-5-yl)-chloroacetamide 8.0 g of N-propargyl-N-(4,6-dimethyl-2-dimethylamino-pyrimidin-5-yl)-hydroxyacetamide, 3.7 g 4-dimethylaminopyridine and 100 ml dry $CH_2Cl_2$ are charged in a sulphonation flask. Thereto are added, dropwise, 3.43 g mesyl chloride in 30 ml of dry $CH_2Cl_2$. The reaction temperature rises from 22° up to 33°. The mixture is heated under reflux for 34 hours, cooled and diluted with water. The organic phase is partitioned off, dried over $Na_2SO_4$ and evaporated. The oily residue is chromatographed on silica gel with diethylether/hexane 1:1 to give the title compound, m.p. 108°–110°.

Example 2

(process b)

N-Propargyl-N-(4,6-dimethylpyrimidin-5-yl)-chloroacetamide

A mixture of 5.0 g (0.025 mol) N-(4,6-dimethyl-pyrimidin-5-yl)-chloroacetamide and 1.0 g tetrabutylammoniumchloride in 150 ml $CH_2Cl_2$ and 6.0 g propargylbromide is cooled to 8°, and 15 ml 50% aqueous NaOH are added dropwise thereto, whereby the temperature gradually rises to 20°. The reaction temperature is maintained at 18° to 20° with cooling. The mixture is stirred during 2½ hours and then diluted with 100 ml $H_2O$. The organic phase is separated off and dried over $Na_2SO_4$. The dried solution is evaporated to give a brown powder that is chromatographed on silica gel with the aid of diethylether (Rf=0.15), yielding the title compound in the form of white crystals m.p. 122°–123°.

Example 3

(process b)

N-(1-Pyrazolylmethyl)-N-(4,6-dimethoxypyrimidin-5-yl)-chloroacetamide 347 g of N-(4,6-dimethoxypyrimidin-5-yl)-chloroacetamide, 60 g benzyltriethylammoniumchloride, 3 l $CH_2Cl_2$ and 252 g 1-pyrazolylmethylchloride are charged in a sulphonation flask and thereto added, quickly, 750 ml 30% aqueous NaOH (w/w) while cooling on a ice bath. The reaction temperature rises from 13° to 25°. The reaction mixture is further stirred under continued cooling on the ice bath until the temperature reaches 23°. Then the ice bath is removed and the reaction is stirred further for 2 hours. The reaction mixture is then diluted with 1.5 l of water and stirred. The organic phase is partitioned off, dried with $Na_2SO_4$ and filtered over a 6 cm $SiO_2$ layer. The $SiO_2$-layer is washed with 10 l diethylether. The resulting reaction mixture is concentrated to 1.5 l and the precipitate, which has been falling out is filtered off and washed with pentane, then it is dried under vacuum at 50° to give the title compound m.p. 117°–119°.

Example 4

(process c)

N-[1-methyl-(ethoxyimino)ethyl]-N-(4,6-dimethoxy-pyrimidin-5-yl)-chloroacetamide (cpd. 64 of Table I)

12.7 g N-[1-methyl-(ethoxyimino)ethyl]-4,6-dimethoxy-pyrimidine-5-amine and 150 ml dry $CH_2Cl_2$ are charged in a sulphonation flask. Thereto are added, dropwise, 6.2 g chloracetylchloride in 25 ml dry $CH_2Cl_2$. The reaction temperature rises from 22° to 28°. The reaction mixture is heated under reflux for 2 hours and cooled. Then 10% aqueous NaOH is added, the organic phase partitioned off, dried over $Na_2SO_4$ and evaporated.

The oily residue is chromatographed on silica-gel with diethylether/hexane 1:3 and then with diethylether/hexane 1:1 to give the oily title compound which crystallises, m.p. 82°–84°.

Example 5

N-(1-Pyrazolylmethyl)-N-(4-dimethylamino-6-ethoxypyrimidin-5-yl)-chloroacetamide To a mixture of 12.9 g (0.05 mol) N-(4-dimethylamino-6-ethoxypyrimidin-5-yl)-chloroacetamide and 2 g benzyltriethylammoniumchloride in 150 g of $CH_2Cl_2$ are added 8.4 g (0.055 mol) of 1-pyrazolylmethylchloride-hydrochloride. To this mixture are quickly added 25 ml of 40% NaOH, whereby the temperature rises from 18° to 32°. The mixture is then stirred for 2 hours and diluted with water. The organic phase is separated off and dried over $Na_2SO_4$. The dried solution is evaporated to give an orange oil that is chromatographed on silica gel with the aid of ethylacetate. The thus obtained yellow oil is dissolved in diethylether and crystallised in a deep-freezer. The title compound is obtained in the form of white crystals of m.p. 112°–114°.

Following the procedure of Examples 1 to 5, but employing the appropriate compounds of formula II, when using process (a), or of formula III and IV (wherein L=Br) when using process (b) or of formula V when using process (c), the following compounds of formula Ib $$\underset{R_{11}}{\overset{R_9}{\underset{N}{\overset{N}{\bigvee}}}} \overset{COCH_2Cl}{\underset{Y}{\overset{N}{\diagdown}}} \quad Ib$$

are obtained (Table I) (Rf values are on silica-gel)

TABLE I

| Cpd. | R$_9$ | R$_{10}$ | R$_{11}$ | Y | Characterisation (°; Rf) |
|---|---|---|---|---|---|
| 1 | CH$_3$ | CH$_3$ | H | CH$_2$OC$_2$H$_5$ | Rf = 0.15[1] |
| 2 | CH$_3$ | CH$_3$ | H | CH$_2$C≡CH | m.p. 122–123° |
| 3 | CH$_3$ | CH$_3$ | H | CH$_2$—CBr=CH$_2$ | m.p. 125–127° |
| 4 | CH$_3$ | CH$_3$ | N(CH$_3$)$_2$ | CH$_2$OC$_2$H$_5$ | Rf = 0.15[2] |
| 5 | CH$_3$ | CH$_3$ | N(CH$_3$)$_2$ | CH$_2$—C≡CH | m.p. 108–110° |
| 6 | CH$_3$ | CH$_3$ | N(CH$_3$)$_2$ | CH$_2$C(CH$_3$)=CH$_2$ | m.p. 80–81° |
| 7 | C$_2$H$_5$ | C$_2$H$_5$ | H | CH$_2$C≡CH | m.p. 73–75° |
| 8 | C$_2$H$_5$ | C$_2$H$_5$ | H | CH$_2$—1-pyrazolyl | m.p. 75–78° |
| 9 | N(CH$_3$)$_2$ | CH$_3$ | H | CH$_2$—1-pyrazolyl | m.p. 129–131°[4] |
| 10 | N(CH$_3$)$_2$ | CH$_3$ | H | CH$_2$C≡CH | m.p. 146–148° |
| 11 | N(CH$_3$)$_2$ | CH$_3$ | H | CH$_2$OCH$_2$CH=CH$_2$ | m.p. 77–79° |
| 12 | N(CH$_3$)(C$_6$H$_5$) | CH$_3$ | H | CH$_2$C≡CH | m.p. 151–153° |
| 13 | N(CH$_3$)(C$_6$H$_5$) | CH$_3$ | H | CH$_2$—1-pyrazolyl | m.p. 191–193° |
| 14 | OCH$_3$ | CH$_3$ | H | CH$_2$C≡CH | m.p. 104–105° |
| 15 | OCH$_3$ | CH$_3$ | H | CH$_2$—1-pyrazolyl | m.p. 101–103° |
| 16 | OCH$_3$ | CH$_3$ | H | CH$_2$OC$_2$H$_5$ | |
| 17 | OCH$_3$ | CH$_3$ | Cl | CH$_2$C≡CH | m.p. 101–103° |
| 18 | OCH$_3$ | CH$_3$ | OCH$_3$ | CH$_2$C≡CH | m.p. 130–132° |
| 19 | OCH$_3$ | CH$_3$ | OCH$_3$ | CH$_2$—1-pyrazolyl | m.p. 148–153° |
| 20 | OC$_4$H$_9$n | CH$_3$ | H | CH$_2$C≡H | Rf = 0.05[2] |
| 21 | OC$_4$H$_9$n | CH$_3$ | H | CH$_2$—1-pyrazolyl | m.p. 67–69° |
| 22 | OCH$_3$ | OCH$_3$ | H | CH$_2$Cl | m.p. 140–142° |
| 23 | OCH$_3$ | OCH$_3$ | H | CH$_2$CH$_2$Cl | m.p. 112–114° |
| 24 | OCH$_3$ | OCH$_3$ | H | CH$_2$CH$_2$Br | m.p. 118–120° |
| 25 | OCH$_3$ | OCH$_3$ | H | CH$_2$CH=CH$_2$ | m.p. 85–87° |
| 26 | OCH$_3$ | OCH$_3$ | H | CH$_2$—C(CH$_3$)=CH$_2$ | m.p. 100–102° |
| 27 | OCH$_3$ | OCH$_3$ | H | CH$_2$—CCl=CH$_2$ | m.p. 78–80° |
| 28 | OCH$_3$ | OCH$_3$ | H | CH$_2$—CBr=CH$_2$ | m.p. 88–90° |
| 29 | OCH$_3$ | OCH$_3$ | H | CH$_2$C≡CH | m.p. 121–123° |
| 30 | " | " | " | CH$_2$C≡C—CH$_2$Cl | m.p. 103–105° |
| 31 | " | " | " | CH$_2$—cyclopropyl(Cl,Cl) | m.p. 85–86° |
| 32 | " | " | " | CH$_2$COOC$_2$H$_5$ | m.p. 61–63° |
| 33 | " | " | " | CH$_2$CON(CH$_3$)$_2$ | |
| 34 | " | " | " | CH$_2$CON(CH$_2$CH=CH$_2$)$_2$ | m.p. 79–81° |
| 35 | " | " | " | CH$_2$—1-pyrazolyl | m.p. 117–119° |
| 36 | " | " | " | CH$_2$—N(pyrazolyl) | |
| 37 | " | " | " | CH$_2$—2-thiazolyl | |
| 38 | " | " | " | CH$_2$—thiazolyl | |
| 39 | " | " | " | CH$_2$—thiazolyl | m.p. 103–105° |
| 40 | " | " | " | CH$_2$—isoxazolyl | m.p. 130–132° |

TABLE I-continued

| Cpd. | R$_9$ | R$_{10}$ | R$_{11}$ | Y | Characterisation (°; Rf) |
|---|---|---|---|---|---|
| 41 | " | " | " | (CH$_2$-oxadiazole ring, N-N with O) | m.p. 144–147° |
| 42 | " | " | " | (CH$_2$-isoxazole ring with CH$_3$) | m.p. 129–133° |
| 43 | " | " | " | (CH$_2$-isoxazole ring with C$_2$H$_5$) | m.p. 93–95° |
| 44 | " | " | " | (CH$_2$-thiadiazole ring, N–S–N) | |
| 45 | " | " | " | (CH$_2$–N-triazole) | m.p. 131–133° |
| 46 | " | " | " | CH$_2$—2-thienyl | m.p. 102–104° |
| 47 | " | " | " | CH$_2$—2-pyrimidinyl | m.p. 173–175° |
| 48 | " | " | " | (CH$_2$–2-pyrimidinyl with CH$_3$) | |
| 49 | " | " | " | CH$_2$OCH$_3$ | m.p. 89–91° |
| 50 | " | " | " | CH$_2$OC$_2$H$_5$ | m.p. 73–75° |
| 51 | " | " | " | CH$_2$OC$_3$H$_7$—n | |
| 52 | " | " | " | CH$_2$OC$_3$H$_7$—i | m.p. 74–76° |
| 53 | " | " | " | CH$_2$OC$_4$H$_9$—n | m.p. 53–55° |
| 54 | " | " | " | CH$_2$O(CH$_2$)$_2$OCH$_3$ | m.p. 80–83° |
| 55 | " | " | " | CH$_2$OCH$_2$CH=CH$_2$ | m.p. 83–85° |
| 56 | " | " | " | CH$_2$OCH$_2$C≡CH | m.p. 122–124° |
| 57 | " | " | " | CH$_2$CH$_2$OCH$_3$ | m.p. 79–81° |
| 58 | " | " | " | CH$_2$CH$_2$OC$_2$H$_5$ | m.p. 74–76° |
| 59 | " | " | " | CH(CH$_3$)CH$_2$OCH$_3$ | |
| 60 | " | " | " | CH$_2$CH=NOCH$_3$ | m.p. 83–85° |
| 61 | " | " | " | CH$_2$C(CH$_3$)=NOCH$_3$ | m.p. 103–105° |
| 62 | " | " | " | CH$_2$C(CH$_3$)=NOC$_2$H$_5$ | m.p. 82–84° |
| 63 | " | " | " | CH$_2$CH=NOC$_2$H$_5$ | m.p. 90–92° |
| 64 | " | " | " | CH(CH$_3$)CH=NOC$_2$H$_5$ | m.p. 82–84° |
| 65 | " | " | " | CH$_2$—CH=C=CH$_2$ | |
| 66 | " | " | " | CH$_2$N(CH$_3$)COCH$_3$ | |
| 67 | " | " | " | (CH$_2$–N pyrazolidinone ring) | |
| 68 | " | " | " | (CH$_2$–N benzothiazolone with Cl) | |
| 69 | OCH$_3$ | OCH$_3$ | CH$_3$ | CH$_2$—1-pyrazolyl | m.p. 136–138° |
| 70 | OCH$_3$ | OCH$_3$ | CH$_3$ | CH$_2$C≡CH | m.p. 103–106° |
| 71 | OC$_2$H$_5$ | OC$_2$H$_5$ | H | CH$_2$C≡CH | m.p. 75–77° |
| 72 | OC$_2$H$_5$ | OC$_2$H$_5$ | H | CH$_2$—1-pyrazolyl | m.p. 102–104° |

TABLE I-continued

| Cpd. | R9 | R10 | R11 | Y | Characterisation (°; Rf) |
|---|---|---|---|---|---|
| 73 | OC2H5 | OC2H5 | H | 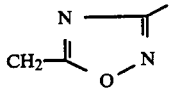 | m.p. 100–101° |
| 74 | OC3H7i | OC3H7i | H | CH2—1-pyrazolyl | m.p. 89–91° |
| 75 | OC3H7n | OC3H7n | H | CH2—1-pyrazolyl | m.p. 82–83° |
| 76 | OC4H9n | OC4H9n | H | CH2C≡CH | Rf = 0.45$^{(2)}$ |
| 77 | OC4H9n | OC4H9n | H | CH2—1-pyrazolyl | m.p. 51–52° |
| 78 | N(CH3)2 | OCH3 | H | CH2C≡CH | m.p. 112–114° |
| 79 | N(CH3)2 | OCH3 | H | CH2OCH2CH=CH2 | m.p. 86–88° |
| 80 | N(CH3)2 | OCH3 | H | CH2—1-pyrazolyl | m.p. 89–91° |
| 81 | N(CH3)2 | OCH3 | H | 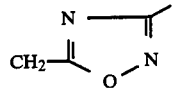 | m.p. 139–141° |
| 82 | N(C2H5)2 | OCH3 | H | CH2—1-pyrazolyl | Oil, Rf = 0.2$^{(1)}$ |
| 83 | N(C2H5)2 | OC2H5 | H | CH2—1-pyrazolyl | Oil, Rf = 0.3$^{(1)}$ |
| 84 | N(CH3)C4H9n | OCH3 | H | CH2C≡CH | Rf = 0.2$^{(2)}$ |
| 85 | " | " | H | CH2—1-pyrazolyl | m.p. 80–82° |
| 86 | Cl | OCH3 | H | CH2—C≡CH | m.p. 89–91° |
| 87 | Cl | OCH3 | H | CH2—1-pyrazolyl | m.p. 125–128° |
| 88 | Cl | OCH3 | H | CH2—2-pyrimidinyl | m.p. 117–119° |
| 89 | Cl | OCH3 | H | CH2CH(CH3)=NOCH3 | m.p. 83–86° |
| 90 | Cl | OC4H9n | H | CH2C≡CH | Rf = 0.32$^{(2)}$ |
| 91 | Cl | OC4H9n | H | CH2—1-pyrazolyl | m.p. 73–76° |
| 92 | Cl | OC4H9n | H | CH2OCH2CH=CH2 | Rf = 0.15$^{(3)}$ |
| 93 | OCH3 | SCH3 | H | CH2C≡CH | m.p. 87–89π |
| 94 | OCH3 | SCH3 | H | CH2—1-pyrazolyl | m.p. 127–130° |
| 95 | OCH3 | SCH3 | H | CH2OC2H5 | m.p. 83–85° |
| 96 | OCH3 | SCH3 | H | CH2OCH2CH=CH2 | m.p. 87–89° |
| 97 | SCH3 | SCH3 | H | CH2C≡CH | m.p. 138–141° |
| 98 | SCH3 | SCH3 | H | CH2—1-pyrazolyl | m.p. 172–174° |
| 99 | SCH3 | SCH3 | H | CH2—2-pyrimidinyl | m.p. 160–162° |
| 100 | SCH3 | SCH3 | H | CH2OC2H5 | m.p. 122–123° |
| 101 | SCH3 | CH3 | H | CH2OC2H5 | |
| 102 | SCH3 | N(CH3)2 | H | CH2—1-pyrazolyl | |
| 103 | OCH3 | H | H | CH2C≡CH | m.p. 94–96° |
| 104 | N(CH3)2 | N(CH3)2 | H | CH2—1-pyrazolyl | |
| 105 | N(CH3)2 | N(CH3)2 | H | CH2C≡CH | m.p. 80–82° |
| 106 | N(CH3)2 | Cl | H | CH2—1-pyrazolyl | m.p. 149–151° |
| 107 | 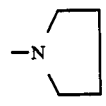 | OCH3 | H | " | m.p. 112–114° |
| 108 | N(CH3)2 | allyloxy | H | " | m.p. 91–94° |
| 109 | N(CH3)2 | 2-methyl-allyloxy | H | " | m.p. 70–72° |
| 110 | N(CH3)2 | OCH2C≡CH | H | " | m.p. 116–118° |
| 111 | N(CH3)2 | O—nC3H7 | H | " | m.p. 117–119° |
| 112 | N(CH3)2 | O—iC3H7 | H | " | m.p. 72–75° |
| 113 | N(CH3)2 | O—nC4H9 | H | " | m.p. 89–91° |
| 114 | N(CH3)2 | O—secC4H9 | H | " | m.p. 72–76° |
| 115 | N(CH3)2 | O—iC4H9 | H | " | |
| 116 | N(CH3)2 | O—tertC4H9 | H | " | |
| 117 | N(CH3)2 | O—nC5H11 | H | " | oil |
| 118 | N(CH3)2 | O—(2-C5H11) | H | " | |
| 119 | N(CH3)2 | O—nC6H13 | H | " | |
| 120 | N(CH3)2 | O—CH2C(CH3)3 | H | " | |
| 121 | N(CH3)2 | O—CH2C(C2H5)2—CH3 | H | " | |
| 122 | N(CH3)2 | S—CH3 | H | " | m.p. 113–115° |
| 123 | N(CH3)2 | O—nC4H9 | H | CH2—(3,5-diCH3—1-pyrazolyl) | |
| 124 | N(CH3)2 | O—CH3 | H | " | |

$^{(1)}$ = diethylether;
$^{(2)}$ = diethylether/hexane 1:1;
$^{(3)}$ = diethylether/hexane 1:3
$^{(4)}$ = the acetate addition salt form has a m.p. of 107–112°

INTERMEDIATES

Example 5

N-Propargyl-N-(4,6-dimethyl-2-dimethylaminopyrimidin-5-yl)hydroxyacetamide

33.2 g 5-amino-4,6-dimethyl-2-dimethylaminopyrimidine, 39.6 glycolic acid butyl ester and 5 g NH$_4$Cl are charged in a round bottom flask. The reaction mixture is heated for 6 hours at 225°, cooled, dissolved in CH$_2$Cl$_2$/CH$_3$OH and then chromatographed on silicagel using ethyl acetate as mobile phase.

The thus obtained powder is washed with diethylether/pentane 1:1 and filtered to give N-(4,6-dimethyl-2-dimethylamino)-pyrimidine, m.p. 141°–144°.

22.16 g of the sodium salt of the latter compound, 10.7 g propargylbromide and 150 ml dry toluene are charged in a sulphonation flask. Thereto are added 50 ml dimethylformamide. The reaction temperature rises from 22° to 48°. The mixture is stirred and heated for 3 hours at 110°, then cooled off and sucked off on hyflo (diatomaceous earth), washed with acetone and evaporated. The resulting oil is chromatographed with diethylether/hexane 1:1 to give the title compound, m.p. 128°–130°

Example 6

N-(4,6-dimethoxypyrimidin-5-yl)chloroacetamide

A sulphonation flask is charged with 310 g 5-amino-4,6-dimethoxypyrimidin and 3500 ml dry CH$_2$Cl$_2$. To this mixture is added, within 15 minutes, a solution of 248.6 g chloroacetyl chloride in 400 ml dry CH$_2$Cl$_2$. The reaction is exothermic, the temperature rises from 14° to 32° and a suspension is formed. The reaction mixture is heated under reflux for 2 hours, then cooled to ambient temperature and evaporated till dryness. The solid residue is suspended in 3 l ice water, the suspension adjusted at pH 7–8 with diluted NaOH, cooled to 5° and sucked-off. The precipitate is washed twice with 500 ml ice water and then dried in vacuum at 60° to give the title compound, m.p. 193°–195°.

Example 7

N-[1-methyl-(ethoxyimino)-ethyl]-4,6-dimethoxypyrimidine-5-amine

A sulphonation flask is charged with with 15.5 g of 5-amino-4,6-dimethoxypyrimidine, 150 ml dry dimethylformamide and 13.8 g K$_2$CO$_3$. The reaction mixture is heated at 110° and then 19.8 g BrCH(CH$_3$)-CH=NOC$_2$H$_5$ are slowly added, dropwise. The reaction mixture is stirred for 4 hours, cooled at ambient temperature, sucked off over hyflo, the hyflo washed with acetone and the solution concentrated. The oily residue is chromatographed on a silica-gel column with diethylether/hexane 3:1 as a mobile phase to give the title compound as an orange-reddish oil, Rf=0.45 in diethylether.

Example 8

4,6-Dimethoxy-5-(2-thienylmethylamino)pyrimidine

Acylation of 5-amino-4,6-dimethoxypyrimidine with 2-thiophenecarboxylic acid chloride in CH$_2$Cl$_2$ gives 4,6-dimethoxy-5-(2-thenoylamino)pyrimidine (m.p. 198°–200°).

A suspension of 13.25 g of the latter compound in 50 ml dry toluene is added dropwise to a sulphonation flask charged with 45 ml sodiumdihydro-bis-(2-methoxyethoxy)aluminate and 50 ml dry toluene.

The reaction temperature rises from ambient temperature to 42° and a red solution is formed. The reaction mixture is then stirred for 5 hours and cooled off at 0°. Then are added, dropwise, 25 ml 20% aqueous KOH, the reaction mixture diluted with diethylether, and the organic phase partitioned off, dried over Na$_2$SO$_4$ and concentrated. The oily residue is chromatographed on silica gel (elution with diethylether/hexane 1:3) to give the title compound, Rf=0.5 in diethylether.

Example 9

5-Amino-4,6-dimethylpyrimidine

208 g (0.85 mol) [4,6-dimethyl-2-thiopyrimidin-5-ylazo]benzene are taken up in 2 liters of CH$_3$OH and treated during 23 hours with Raney-Ni/H$_2$ at 20° to 35°. The reaction mixture is filtered and the filtrate evaporated. The remaining dark brown oil is consecutively chromatographed on a silica gel column with ethylacetate and with CH$_2$Cl$_2$/CH$_3$OH 9:1 (Rf=0.25). A brown powder is obtained which is digested with pentane, then filtered and dried to yield the title compound as a brown powder, m.p. 98°–100°.

Example 10

5-Amino-4-diethylamino-6-methoxy-pyrimidine

Step a

In a sulphonation flask are dissolved 17.25 g sodium metal in 1000 ml absolute CH$_3$OH. The reaction mixture is cooled to ambient temperature and then a solution of 116 g 4 -chloro-6-diethylamino-5-nitropyrimidine in 500 ml absolute CH$_3$OH is added dropwise thereto. The reaction temperature rises from 22° to 32°. The reaction mixture is then heated for one hour under reflux. The reaction mixture is cooled and concentrated. The residue is taken up in diethylether, washed with water, the organic phase is partitioned off and dried over Na$_2$SO$_4$, concentrated, chromatographed on a silica gel column (elution with diethylether/hexane 1:10) to give a yellow, clear oil (4-diethylamino-6-methoxy-5-nitropyrimidine), Rf=0.3 in ether/hexane 1:3.

Step b 101.7 g of the latter product are hydrogenated during 16 hours in the presence of 5.1 g Pd/C in 1 l CH$_3$OH at ambient temperature and under normal pressure to yield the title compound which is chromatographed on silicagel (elution with diethylether/hexane 1:1), Rf=0.4 in diethylether.

The following compounds of formula IIa

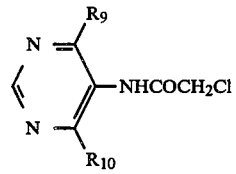

IIa are examples of compounds obtainable analogous to the procedure of Example 6 (Table II).

TABLE II

| Cpd. | R$_9$ | R$_{10}$ | Characterisation (m.p.) |
| --- | --- | --- | --- |
| Z1 | CH$_3$ | CH$_3$ | 108–111° |
| Z2 | C$_2$H$_5$ | C$_2$H$_5$ | 137–138° |
| Z3 | N(CH$_3$)$_2$ | CH$_3$ | 114–116° |

TABLE II-continued

| Cpd. | $R_9$ | $R_{10}$ | Characterisation (m.p.) |
|---|---|---|---|
| Z4  | $N(CH_3)C_6H_5$ | $CH_3$ | 164–166° |
| Z5  | $OCH_3$ | $CH_3$ | 125–127° |
| Z6  | $OC_4H_9n$ | $CH_3$ | 94–97° |
| Z7  | $OCH_3$ | $OCH_3$ | 193–195° |
| Z8  | $OC_2H_5$ | $OC_2H_5$ | 153–154° |
| Z9  | $OC_3H_7i$ | $OC_3H_7i$ | 152–153° |
| Z10 | $OC_4H_9n$ | $OC_4H_9n$ | 109–110° |
| Z11 | $N(CH_3)_2$ | $OCH_3$ | 144–146° |
| Z12 | $N(C_2H_5)_2$ | $OCH_3$ | 125–127° |
| Z13 | $N(C_2H_5)_2$ | $OC_2H_5$ | 132–134° |
| Z14 | $N(CH_3)C_4H_9n$ | $OCH_3$ | 126–128° |
| Z15 | $Cl$ | $OCH_3$ | 136–138° |
| Z16 | $Cl$ | $OC_4H_9n$ | 104–106° |
| Z17 | $OCH_3$ | $SCH_3$ | 174–177° |
| Z18 | $SCH_3$ | $SCH_3$ | 200–202° |
| Z19 | $OCH_3$ | $H$ | 101–103° |
| Z20 | $N(CH_3)_2$ | $N(CH_3)_2$ | 161° (decomp.) |
| Z21 | $n\text{-}C_3H_7O$ | $n\text{-}C_3H_7O$ | 118–119° |

The following compounds of formula VIa

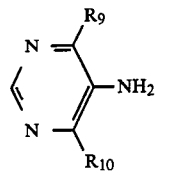

VIa are examples of compounds obtainable according to the procedure of Example 10 (step b)—Table III.

TABLE III

| Cpd. | $R_9$ | $R_{10}$ | Characterisation (°; Rf) |
|---|---|---|---|
| A1  | $CH_3$ | $CH_3$ | 98–100° |
| A2  | $C_2H_5$ | $C_2H_5$ | 76–79° |
| A3  | $N(CH_3)_2$ | $CH_3$ | 130–132° |
| A4  | $N(CH_3)C_6H_5$ | $CH_3$ | 87–89° |
| A5  | $OCH_3$ | $CH_3$ | 65–67° |
| A6  | $OC_4H_9n$ | $CH_3$ | $Rf = 0.15^{(1)}$ |
| A7  | $OCH_3$ | $OCH_3$ | 94–96° |
| A8  | $OC_2H_5$ | $OC_2H_5$ | 63–65° |
| A9  | $OC_3H_7n$ | $OC_3H_7n$ | 42–43° |
| A10 | $OC_3H_7i$ | $OC_3H_7i$ | $Rf = 0.4^{(2)}$; 57–59° |
| A11 | $OC_4H_9n$ | $OC_4H_9n$ | 77–79° |
| A12 | $N(CH_3)_2$ | $OCH_3$ | 77–79° |
| A13 | $N(C_2H_5)_2$ | $OCH_3$ | $Rf = 0.4^{(1)}$ |
| A14 | $N(C_2H_5)_2$ | $OC_2H_5$ | $Rf = 0.3^{(2)}$ |
| A15 | $N(CH_3)C_4H_9n$ | $OCH_3$ | $Rf = 0.45^{(1)}$ |
| A16 | $Cl$ | $OCH_3$ | 73–75° |
| A17 | $Cl$ | $OC_4H_9n$ | 37–38° |
| A18 | $OCH_3$ | $SCH_3$ | 69–71° |
| A19 | $SCH_3$ | $SCH_3$ | 82–83° |
| A20 | $SCH_3$ | $CH_3$ | 83–84° |
| A21 | $OCH_3$ | $H$ | 71–73° |
| A22 | $N(CH_3)_2$ | $N(CH_3)_2$ | 84–86° |
| A23 | $OCH_3$ | $OC_3H_7i$ | 57–59° |

$^{(1)}$ = diethylether;
$^{(2)}$ = diethylether/hexane 1:1

TEST RESULTS

Test Example 1

Weed control—Pre-emergence Treatment

Seed pots (7 cm diameter) are filled with a mixture of peat culture substrate and sand. The exposed surface of the peat culture substrate and sand mixture is sprayed with a test liquid of a test compound (e.g. formulated in accordance with Example B) and seeds of *Lepidium sativum, Agrostis alba, Avena sativa* and *Lolium perenne* are sown in each pot, whereby the *Avena sativa* and *Lolium perenne* seeds are, after sowing covered with a thin layer (0.5 cm) of peat culture substrate/sand mixture. The pots are kept for 21 days at room temperature with 14 to 17 hours light (daylight or its equivalent) per day.

Determination of the herbicidal effect of the particular herbicide is made after the 21 day period. The determination involves a visual evaluation of the degree and quality of damage to the various seed plants.

The compounds of formula I of Table I are applied in the above manner at dosages equivalent to 1.4 and 5.6 kg of active agent/hectare.

Herbicidal activity is observed, that is to say, significant damage to the test plants is observed.

Test Example 2

Weed control—Post-emergence Treatment

A procedure similar to that employed in Test Example 1 is followed with the exception that the test compounds (herbicides) are applied when the plants are at the 2–4 leaf stage, the sowing of the plant seeds being staggered to ensure that the plants reach the 2–4 leaf stage at about the same time.

Again the compounds of Table I are applied in the above manner at dosages corresponding to 1.4 kg/ha and 5.6 kg/ha. The determination of the herbicidal effect is made 21 days after application of the test compounds and involves an analogous evaluation as described in Test Example 1. Herbicidal activity is observed.

Test Example 3

The following Table A will reflect a further evaluation of a representative compound of the invention in the following test procedure.

The pre-emergence activity is established with the aid of seed dishes measuring 30×40 cm, filled to a depth of 6 cm with a mixture of peat culture substrate and sand. The exposed surface of the peat culture substrate and sand mixture is sprayed with an aqueous test liquid (e.g. formulated in accordance with Example B) comprising a compound of the invention in a given concentration. The spray volume corresponds to 600 l aqueous test liquid/ha. The same test is repeated with various concentrations of test liquid, whereby the concentrations are selected in such a manner that the application rates indicated on the following table are realised. Six species of seed are then sown in each dish. The number of seeds sown for each plant species depends on the seed germination potential and also the initial growth size of the particular seed plant. After sowing of the seeds, the treated surface is covered with a thin layer about 0.5 cm deep of the peat culture and sand mixture.

The prepared seed dishes are kept for 28 days at a temperature of 20° to 24° C. and 14 to 17 hours light each day.

The post-emergence activity is established analogously, except that the herbicide test liquid is applied when the plants are at a 2–4 leaf stage.

Determination of the herbicidal effect of the particular herbicide is made 28 days after application of the test compound. The determination involves a visual evaluation of the degree and quality of damage to the various seed plants.

TABLE A

| | Compound 35 | | Standard** | | |
|---|---|---|---|---|---|
| | pre-em | post-em | pre-em | | post-em |
| Plant treated | kg/ha | | | | |
| | 1 | 5 | 5 | 1 | 5 | 5 |
| *Amaran. retrofl.* | 90 | 100 | 100 | 80 | 90 | 60 |
| *Capsella b.p.* | 90 | 90 | 90 | 30 | 80 | 90 |
| *Chenop. alb.* | 90 | 90 | 100 | 0 | 60 | 20 |
| *Galium aparine* | 90 | 90 | 90 | 10 | 30 | 60 |
| *Senecio vulg.* | 90 | 100 | 100 | 10 | 90 | 100 |
| *Stellaria media* | 90 | 90 | 30 | 0 | 30 | 10 |
| Alfalfa | 90 | 90 | 90 | 50 | 90 | 60 |
| Bean | 60 | 80 | 80 | 0 | 0 | 40 |
| Carrot | 90 | 100 | 90 | 0 | 30 | 30 |
| Cotton | 0 | 80 | 90 | 0 | 0 | 40 |
| Flax | 10 | 10 | 100 | 10 | 10 | 70 |
| Potato | 0 | 0 | 20 | 0 | 0 | 20 |
| Soya | 30 | 90 | 80 | 0 | 0 | 20 |
| Sugar beet | 0 | 20 | 20 | 0 | 0 | 0 |
| Rape | 0 | 10 | 50 | 0 | 0 | 30 |
| Sunflower | 0 | 10 | 60 | 30 | 0 | 60 |
| *Agropyron repens* | 90 | 90 | 50 | 90 | 100 | 0 |
| *Agrostis alba* | 100 | 100 | — | 90 | 100 | — |
| *Alopec. myos.* | 90 | 90 | 90 | 20 | 50 | 40 |
| *Apera sp. venti.* | 100 | 100 | 100 | 100 | 100 | 90 |
| *Avena fatua* | 80 | 90 | 90 | 10 | 40 | 60 |
| *Echinochloa c.g.* | 90 | 100 | 90 | 90 | 90 | 90 |
| Corn | 90 | 100 | 80 | 0 | 10 | 50 |
| Wheat | 100 | 100 | 70 | 20 | 100 | 0 |

**2-Chloro-N—(2-ethyl-6-methylphenyl)-N—(2-methoxy-1-methyl-ethyl)-acetamide
— = not tested

Test Example 4

Persistence

The persistence of the test compounds is investigated in arable soil, wherein seeds are sown 21 days after treatment with the test compound (application rate: 1 kg/ha).

The visual evaluation of the degree and quality of herbicidal activity is effected 28 days after application of the test substance.

The compounds have an appropriate persistence as illustrated in the following table for a representative compound (Compound 35) in comparison with 2-chloro-N-(2-ethyl-6-methyl-phenyl)-N-(2-methoxy-1-methylethyl)acetamide as a standard—see Table B.

TABLE B

| | % damage | |
|---|---|---|
| Test compound | Compound 35 | Standard |
| Corn (Mais) | 0 | 0 |
| Agrostis | 85 | 90 |
| Alopecurus | 85 | 80 |
| Setaria | 90 | 90 |
| *Poa annua* | 85 | 90 |
| *Echinochloa crus galli* | 90 | 90 |

Test Example 5

Field Performance

The efficacy of the compounds of the invention is evaluated in the field in that weed and crop species are planted in rows which then are treated either immediately afterwards (for pre-emergence activity) or at the 2–4 leaf stage of the emerged plants (for early post-emergence activity). The rates are 0.5 and 1.5 kg active ingredient/ha and are applied at a volume of 750 l/ha. The degree and quality of activity is evaluated visually 28–42 days after treatment. The compounds show good herbicidal activity and also good crop tolerance as shown in the following Tables (C and D) for a representative compound (Compound No. 35). The standard material is 2-chloro-N-(2-ethyl-6-methyl-phenyl)-N-(2-methoxy-1-methylethyl)-acetamide.

TABLE C

| Activity after pre-em application | | | | |
|---|---|---|---|---|
| Test Compound | Compound No. 35 | | Standard | |
| Rate (kg//ha) | 0.5 | 1.5 | 0.5 | 1.5 |
| Plant species | % damage | | | |
| Corn | 0 | 0 | 0 | 10 |
| Wheat | 0 | 0 | 0 | 0 |
| Sugar Beet | 0 | 0 | 10 | 0 |
| Soybean | 0 | 0 | 0 | 0 |
| Potato | 0 | 0 | 0 | 0 |
| Rape | 0 | 0 | 0 | 0 |
| *Avena fatua* | 20 | 40 | 0 | 0 |
| *Poa annua* | 0 | 80 | 0 | 70 |
| *Alopecurus myosuroides* | 20 | 90 | 10 | 30 |
| *Echinochloa crus-galli* | 10 | 85 | 40 | 98 |
| *Galium aparine* | 0 | 50 | 0 | 0 |
| *Amaranthus retroflexus* | 20 | 30 | 0 | 50 |

TABLE D

| Activity after early post-em application | | | | |
|---|---|---|---|---|
| Test Compound | Compound No. 35 | | Standard | |
| Rate (kg//ha) | 0.5 | 1.5 | 0.5 | 1.5 |
| Plant species | % damage | | | |
| Corn | 0 | 20 | 0 | 0 |
| Wheat | 10 | 40 | 0 | 0 |
| Sugar Beet | 0 | 5 | 0 | 0 |
| Soybean | 0 | 40 | 0 | 5 |
| Potato | 0 | 10 | 0 | 0 |
| Rape | 0 | 10 | 0 | 0 |
| *Avena fatua* | 10 | 10 | 10 | 0 |
| *Poa annua* | 80 | 90 | 0 | 0 |
| *Alopecurus myosuroides* | 20 | 90 | 0 | 10 |
| *Echinochloa crus-galli* | 85 | 95 | 0 | 70 |
| *Galium aparine* | 90 | 100 | 10 | 40 |
| *Amaranthus retroflexus* | 30 | 60 | 0 | 0 |

Test Example 6

Use against Perennial Weeds

N-(4-Dimethylamino-6-methoxy-5-pyrimidinyl)-N-pyrazolylmethylchloroacetamide (hereinafter compound A) is tested under greenhouse conditions (20° daylight—ca. 6000 LUX on average during 16 hours), against Cyperus rotundus, Cynodon dactylon, Agropyron repens, Sorghum halepense and Convolvulus sepium in pots. The herbicidal activity of the test compounds is evaluated after pre-em and post-em spray-application.

For pre-em evaluation the rhizomes are covered with substrate and the test substance is then applied in aqueous spray form.

For post-em evaluation the whole plant (size 20–25 cm) is treated by conventional post-em spray-application.

Beet soil is used as substrate.

The spray-application is effected under 2 conditions (600 l and 2000 l/ha); the results indicated in Table E are an average of 4 tests (2 application conditions, 1 replication).

The result is evaluated 14, 28, 56 and 96 days after application. After the 3 evaluation (56 days after application) the plant is cut back just above the soil level; the growth from the remaining stumps is evaluated 40 days thereafter (i.e. 96 days after application).

The results are as follows:

TABLE E

| Application | pre-em | | | | | | post-em | | | | | |
|---|---|---|---|---|---|---|---|---|---|---|---|---|
| Compound | Compound A | | | Standard I | | | Compound A | | | Standard I | | |
| Dosage kg a.i./ha | 3.0 | 6.0 | 12.0 | 3.0 | 6.0 | 12.0 | 3.0 | 6.0 | 12.0 | 3.0 | 6.0 | 12.0 |
| 14 DAA | | | | | | | | | | | | |
| Convolvulus | 95 | 100 | 100 | 15 | 55 | 70 | 45 | 55 | 60 | 60 | 60 | 60 |
| Agropyron | 95 | 100 | 85 | 10 | 45 | 60 | 25 | 25 | 25 | 55 | 55 | 65 |
| Cynodon dact. | 60 | 70 | 80 | 20 | 25 | 50 | 40 | 45 | 50 | 40 | 45 | 55 |
| Sorghum hal. | 35 | 35 | 40 | 45 | 55 | 60 | 20 | 30 | 35 | 45 | 45 | 50 |
| Cyperus rot. | 40 | 40 | 45 | 10 | 20 | 35 | 10 | 10 | 10 | 10 | 20 | 30 |
| 28 DAA | | | | | | | | | | | | |
| Convolvulus | 90 | 95 | 100 | 20 | 35 | 55 | 50 | 70 | 80 | 60 | 60 | 70 |
| Apropyron | 95 | 100 | 100 | 15 | 50 | 70 | 55 | 55 | 60 | 85 | 90 | 90 |
| Cynodon | 80 | 90 | 90 | 35 | 45 | 75 | 50 | 60 | 60 | 50 | 55 | 65 |
| Sorghum hal. | 60 | 75 | 75 | 20 | 60 | 65 | 50 | 60 | 65 | 60 | 65 | 70 |
| Cyperus rot. | 65 | 70 | 70 | 20 | 30 | 45 | 20 | 25 | 35 | 25 | 25 | 45 |
| 56 DAA (prior to cutting back) | | | | | | | | | | | | |
| Convolvulus | 60 | 70 | 95 | 15 | 30 | 35 | 65 | 70 | 75 | 40 | 45 | 65 |
| Agropyron rep. | 100 | 100 | 100 | 10 | 45 | 55 | 75 | 85 | 100 | 75 | 95 | 100 |
| Cynodon dact. | 75 | 85 | 95 | 20 | 40 | 65 | 70 | 75 | 85 | 50 | 60 | 70 |
| Sorghum hal. | 65 | 75 | 90 | 10 | 10 | 10 | 60 | 75 | 80 | 60 | 75 | 80 |
| Cyperus rot. | 65 | 75 | 85 | 0 | 10 | 20 | 60 | 80 | 90 | 55 | 70 | 80 |
| 96 DAA (inhibition of regrowth) | | | | | | | | | | | | |
| Convolvulus | 10 | 10 | 10 | 0 | 10 | 0 | 0 | 0 | 0 | 0 | 10 | 15 |
| Agropyron rep. | 100 | 100 | 100 | 0 | 60 | 75 | 60 | 100 | 100 | 75 | 95 | 100 |
| Cynodon dact. | 85 | 95 | 100 | 0 | 15 | 60 | 100 | 100 | 100 | 10 | 50 | 100 |
| Sorghum hal. | 75 | 75 | 95 | 0 | 50 | 75 | 20 | 30 | 35 | 20 | 35 | 60 |
| Cyperus rot. | 45 | 60 | 85 | 0 | 0 | 0 | 0 | 35 | 65 | 40 | 80 | 90 |

DAA = days after application /
a.i. = active ingredient
Standard I = mixture comprising 240 g/l aminotriazole + 215 g/l ammoniumthiocyanate

Test Example 7

The herbicidal activity of the compound of Example 5 and of Compounds 106, 107 and 108 (Table I hereinbefore) is tested after post-em application under conditions as indicated in Test Example 6 hereinbefore except that the compounds are only applied at a spray-volume equivalent to 600 l/ha. The results indicated in Table F are the average of 2 tests.

Metolachlor was used as standard.

TABLE F

Greenhouse - post-em trials

| Examples | 1 | | | 2a | | | 2b | | | 2c | | | Metolachlor | | |
|---|---|---|---|---|---|---|---|---|---|---|---|---|---|---|---|
| Dosage kg a.i./ha | 3.0 | 6.0 | 12.0 | 3.0 | 6.0 | 12.0 | 3.0 | 6.0 | 12.0 | 3.0 | 6.0 | 12.0 | 3.0 | 6.0 | 12.0 |
| 14 DAA | | | | | | | | | | | | | | | |
| Convolvulus sep. | 20 | 45 | 50 | 40 | 50 | 50 | 40 | 40 | 50 | 40 | 45 | 45 | 15 | 20 | 30 |
| Agropyron rep. | 5 | 40 | 45 | 25 | 25 | 30 | 15 | 30 | 35 | 25 | 30 | 30 | 15 | 35 | 45 |
| Cynodon dact. | 15 | 20 | 25 | 20 | 40 | 45 | 15 | 20 | 30 | 20 | 20 | 20 | 20 | 20 | 30 |
| Sorghum hal. | 0 | 0 | 0 | 0 | 0 | 0 | 0 | 0 | 10 | 10 | 10 | 15 | 0 | 0 | 30 |
| Cyperus rot. | 5 | 10 | 10 | 0 | 15 | 30 | 0 | 20 | 30 | 10 | 10 | 30 | 10 | 15 | 35 |
| 28 DAA | | | | | | | | | | | | | | | |
| Convolvulus sep. | 20 | 60 | 60 | 35 | 45 | 60 | 40 | 45 | 60 | 50 | 55 | 60 | 10 | 20 | 30 |
| Agropyron rep. | 30 | 35 | 50 | 35 | 45 | 45 | 30 | 45 | 45 | 35 | 40 | 50 | 40 | 50 | 55 |
| Cynodon dact. | 40 | 45 | 50 | 40 | 55 | 55 | 30 | 35 | 35 | 45 | 50 | 50 | 25 | 35 | 40 |
| Sorghum hal. | 0 | 20 | 25 | 0 | 0 | 15 | 0 | 20 | 25 | 20 | 20 | 25 | 0 | 0 | 0 |
| Cyperus rot. | 25 | 30 | 30 | 30 | 40 | 60 | 25 | 30 | 30 | 30 | 30 | 45 | 20 | 25 | 35 |
| 56 DAA (prior to cutting back) | | | | | | | | | | | | | | | |
| Convolvulus sep. | 20 | 55 | 70 | 35 | 55 | 60 | 40 | 55 | 60 | 40 | 55 | 70 | 20 | 40 | 45 |
| Agropyron rep. | 60 | 75 | 85 | 80 | 90 | 90 | 70 | 80 | 80 | 70 | 85 | 90 | 60 | 80 | 80 |
| Cynodon dact. | 60 | 60 | 70 | 60 | 70 | 70 | 45 | 60 | 60 | 60 | 65 | 70 | 50 | 50 | 50 |
| Sorghum hal. | 0 | 30 | 70 | 10 | 40 | 50 | 15 | 40 | 70 | 20 | 30 | 75 | 0 | 0 | 10 |
| Cyperus rot. | 50 | 60 | 65 | 55 | 70 | 75 | 50 | 55 | 85 | 55 | 75 | 80 | 20 | 45 | 60 |
| 96 DAA (% inhibition of regrowth) | | | | | | | | | | | | | | | |
| Convolvulus sep. | 0 | 40 | 60 | 0 | 50 | 70 | 0 | 30 | 30 | 0 | 0 | 25 | 0 | 0 | 0 |
| Agropyron rep | 15 | 100 | 100 | 100 | 100 | 100 | 75 | 100 | 100 | 100 | 100 | 100 | 50 | 85 | 100 |
| Cynodon dact. | 50 | 100 | 100 | 100 | 100 | 100 | 100 | 100 | 100 | 100 | 100 | 100 | 45 | 60 | 100 |
| Sorghum hal. | 50 | 90 | 100 | 20 | 70 | 70 | 20 | 80 | 100 | 20 | 70 | 100 | 0 | 0 | 35 |
| Cyperus rot. | 60 | 100 | 100 | 50 | 100 | 100 | 0 | 95 | 100 | 90 | 100 | 100 | 0 | 30 | 30 |

Test Example 8

Greenhouse test (post-em)

Cyperus esculentus plants (ca. 25 cm) obtained from single tubers grown in seed pots filled with beet soil are treated with a spray solution of a compound of formula I at a rate equivalent to an application rate of 8 kg, 16 kg and 24 kg/ha (spray solume equivalent to 600 l/ha.)

Analogous tests are run with Cyperus rotundus (size ca. 25 cm) except that the application rates are equivalent to 16 kg and 24 kg.

The damage is determined after visual evaluation 14 days, 28 days and 56 days after application. The day of the 3rd determination (56 days after application) the plants are cut back and the inhibition of regrowth is then expressed 96 days after application. At the same day (96 DAA) the number of new developed tubers is counted and compared with an untreated standard. It is then determined how many of those newly developed tubers are still capable of shooting.

The results are expressed in Table G in which

---

Compound A is N—(4-dimethylamino-6-methoxy-5-pyrimidinyl)-N—pyrazolyl-methyl-chloroacetamide B is N—[4-(N—n-butyl-N—methylamino)-6-methoxy-5-pyrimidinyl)-N—pyrazolylmethyl-chloroacetamide C is N—(4-diethylamino-6-methoxy-5-pyrimidinyl)-N—pyrazolyl-methyl-chloroacetamide

--- a.i. is active ingredient.

TABLE G

| | Greenhouse - post-em | | | | | | | | | | | | | | | |
|---|---|---|---|---|---|---|---|---|---|---|---|---|---|---|---|---|
| | Cyperus esculentus | | | | | | | | | | | | Cyperus rotundus | | | |
| Test substance | Compound A | | | Compound B | | | Compound C | | | Metolachlor (Standard) | | | Compound A | | Compound B | | Compound C | |
| kg a.i./h | 8 | 16 | 24 | 8 | 16 | 24 | 8 | 16 | 24 | 8 | 16 | 24 | 16 | 24 | 16 | 24 | 16 | 24 |
| % damage | | | | | | | | | | | | | | | | | | |
| 14 DAA | 10 | 10 | 10 | 0 | 17 | 10 | 7 | 10 | 17 | 0 | 10 | 20 | 0 | 20 | 0 | 0 | 0 | 0 |
| 88 DAA | 37 | 40 | 43 | 30 | 30 | 37 | 30 | 33 | 40 | 30 | 30 | 30 | 50 | 70 | 40 | 40 | 40 | 50 |
| 56 DAA[1] | 87 | 90 | 90 | 73 | 80 | 92 | 80 | 87 | 90 | 0 | 0 | 0 | 70 | 90 | 70 | 70 | 70 | 80 |
| 96 DAA[2] | 100 | 100 | 100 | 50 | 100 | 100 | 100 | 100 | 100 | 0 | 0 | 0 | 100 | 100 | 70 | 100 | 90 | 100 |
| Number of newly generated tubers[3] | 0 | 0 | 0 | 0 | 0 | 0 | 0 | 0 | 0 | 72 | 48 | 24 | 17 | 17 | 26 | 11 | 28 | 22 |
| Number of shooting newly generated tubers | — | — | — | — | — | — | — | — | — | — | — | — | 0 | 0 | 4 | 0 | 2 | 0 |

[1]prior to cutting back
[2]inhibition of regrowth in % of non-treated control
[3]in the non-treated control the number was 125 (cyperus esculentus and 85 (cyperus rotundus; 30 thereof shooting)
— means not evaluated

What is claimed is:

1. A compound of the formula:

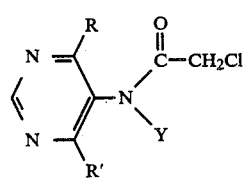

wherein
R and R' are independently F, Cl, Br, $C_{1-4}$alkyl, $C_{1-8}$alkoxy, $C_{3-5}$alkenyloxy, $C_{3-5}$alkinyloxy, $C_{1-8}$alkylthio or di($C_{1-4}$alkyl) amino, and
Y is (a') a hydrocarbon selected from the group consisting of $C_{3-5}$alkenyl and $C_{3-5}$alkinyl, which hydrocarbon is optionally mon-substituted by F, Cl or Br;

(b') $C_{1-3}$alkoxy-$C_{1-3}$alkylene optionally mono-substituted by $C_{1-4}$alkoxy;

(c') $C_{3-5}$alkinoxy-$C_{1-3}$alkylene;

(d') $C_{3-5}$alkenoxy-$C_{1-3}$alkylene;

(e') $CH_2$—CH=CH=$CH_2$;

(f') $CH(R_6')A_z'$
wherein
$R_6'$ is H or $CH_3$ and
$A_z'$ is
  (i) 1-pyrazolyl, 3,5-dimethyl-1-pyrazolyl, 1-imidazolyl, 1,2,3-triazol-1-yl or 1,2,4-triazole-1-yl;
  (ii) a 5-membered aromatic heteroring linked by a C-atom thereof to the $CH(R_6')$ group of $CH(R_6')A_z'$ and having 1 to 3 heteroatoms selected from the group consisting of O, S and N; or
  (iii) 2-pyrimidinyl; such $A_z'$ heteroring being optionally mono- or di-substituted on a ring C-atom thereof by $C_{1-4}$alkyl;

(g') $CHR_5$—$CHR_5'$=NO($C_{1-4}$alkyl);

(h') $CH(R_6)B'$
wherein
B' is
  (i) $N(CH_3)COCH_3$; or
  (ii) 2-oxo-3-benzthiazolidinyl optionally mono-substituted by F, Cl or Br; or (i') $CH(R_6)COY_1'$ in which $Y_1'$ is di($C_{1-4}$alkyl)amino or $C_{1-4}$alkoxy,
wherein
$R_5$ and $R_5'$ are independently H or $CH_3$ or $R_5$ together with $R_5'$ are $(CH_2)_3$ or $(CH_2)_4$, and
$R_6$ is H or $C_{1-3}$alkyl,
in free base or in acid addition salt form.

2. A compound of claim 1 in which $A_z'$ is selected from the group consisting of 1,2,4-triazol-1-yl, 2-methyl-1,3,4-oxadiazol-5-yl, 3-methyl-1,2,4-oxadiazol-5-yl, 3-methyl-isoxazol-5-yl, 2-methyl-thiazol-4-yl, 2-thienyl, 2-pyrimidinyl and 1-pyrazolyl.

3. A compound of claim 1 in which at least one of R and R' is $C_{1-4}$alkoxy, di($C_{1-4}$alkyl) amino.

4. A compound of claim 2 in which at least one of R and R' is $C_{1-4}$alkoxy, di($C_{1-4}$alkyl) amino.

5. A compound of claim 4, in which R is $N(CH_3)_2$, $N(C_2H_5)_2$ or $N(CH_3)n$-$C_4H_9$ or 1-pyrrolidinyl and R' is Cl, $C_{1-8}$alkoxy, $C_{3-5}$alkenyloxy, $C_{3-5}$-alkinyloxy or $C_{1-8}$alkylthio.

6. A compound of claim 3 in which Y is A-O-$R_3$ wherein A is $CH_2$ or $(CH_2)_2$ and $R_3$ is $CH_3$, $C_2H_5$, $CH_2CH=CH_2$, $CH_2C\equiv CH$ or $(CH_2)_2OCH_3$.

7. A compound of claim 4 in which Y is $CH(R_6')A_z'$ and $A_z'$ is 1-pyrazolyl.

8. A compound of claim 5 in which Y is $CH(R_6')A_z'$ and $A_z'$ is 1-pyrazolyl.

9. The compound of claim 7 in which each of R and R' is $OCH_3$ and Y is 1-pyrazolylmethyl.

10. A compound of claim 8 in which $R_6'$ is H.

11. A compound of claim 10 in which R' is $C_{1-8}$alkoxy.

12. A compound of claim 11 in which R' is $C_{1-4}$alkoxy.

13. A compound of claim 10 in which R' is $C_{1-4}$alkylthio.

14. The method of combatting weeds in a locus comprising applying to the locus a herbicidally effective amount of a compound as defined in claim 1, in free base form or agriculturally acceptable acid addition salt form.

15. The method of claim 14 in which the locus is a crop locus and the compound is applied in an amount sufficient to combat weeds without substantially damaging the crop.

16. The method of claim 14 in which the locus is a locus infested with perennial weeds.

17. The method of claim 15 in which the compound in which R and R' are each methoxy and Y is 1-pyrazolylmethyl is applied to a crop locus of a crop selected from the group consisting of carrots, cotton, flax, potato, soybean, sugar beet, rape, sunflower, corn and wheat.

18. The method of combatting weeds in a locus comprising applying to the locus a herbicidally effective amount of a compound of the formula:

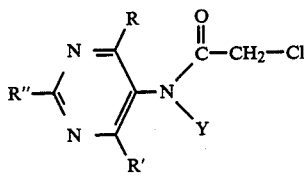

wherein
R, R' and R" are each independently H; F; Cl; Br; $C_{1-4}$alkyl optionally substituted by F, Cl, Br or $C_{1-4}$alkoxy; formyl; $CH=NOCH_3$; $C_{2-4}$alkanoyl; $CH(OC_{1-2}alkyl)_2$; $C_{1-8}$alkylthio; $C_{1-8}$alkoxy; benzyloxy; phenoxy, di($C_{1-4}$alkyl)amino-$C_{1-4}$alkylenoxy; $C_{1-4}$alkoxy-$C_{1-4}$alkylenoxy; $C_{1-4}$alkylthio-$C_{1-4}$alkylenoxy; di-$C_{1-4}$alkylamino or N-$C_{1-4}$alkyl-N-phenylamino; and Y is
(a) a hydrocarbon selected from the group consisting of $C_{1-8}$alkyl, $C_{3-8}$alkyl, $C_{3-8}$alkinyl, $C_{3-8}$cycloalkyl, $C_{5-8}$cycloalkenyl and $C_{3-8}$cycloalkyl-$C_{1-5}$alkyl, which hydrogen is optionally substituted by F, Cl or Br;

(b) a group $CH(R_1)$-$COY_1$, wherein
$R_1$ is H or $C_{1-5}$alkyl and
$Y_1$ is $C_{1-4}$alkoxy or di($C_{1-4}$alkyl)amino;

(c) a group $R_2$-Az,
wherein
$R_2$ is $CH_2$ or $CH_2$-$CH_2$ optionally substituted by $C_{1-5}$alkyl, and Az is a diazole or triazole ring linked by one of its N-atoms to $R_2$ and optionally substituted by $C_{1-5}$alkyl; a 5-membered aromatic heteroring linked by a C-atom thereof to $R_2$, having 1 to 3 heteroatoms selected from the group consisting of O, S and N and optionally substituted by $C_{1-5}$alkyl; or a pyrimidinyl ring linked by a C-atom thereof to $R_2$ and optionally substituted by $C_{1-5}$alkyl, (d) a group A-O-$R_3$;
wherein $R_3$ is H, a hydrocarbon group selected from the group consisting of $C_{1-8}$alkyl, $C_{3-8}$alkenyl, $C_{3-8}$alkinyl, $C_{3-8}$cycloalkyl, $C_{5-8}$cycloalkenyl or $C_{3-8}$cycloalkyl-$C_{1-5}$alkyl, said $R_3$ hydrocarbon group being optionally substituted by F, Cl, Br, $C_{1-4}$alkoxy or 1-pyrazolyl; phenyl; or a group

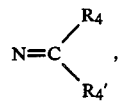

wherein
$R_4$ is a hydrocarbon group selected from the group consisting of $C_{1-5}$alkyl, $C_{3-5}$alkenyl, $C_{3-5}$alkinyl, $C_{3-8}$cycloalkyl, $C_{5-8}$cycloalkeny, $C_{3-8}$cycloalklyl-$C_{1-5}$alkyl, said $R_4$ hydrocarbon being optionally substituted by F, Cl or Br; or $R_4$ is allene,
$R_4'$ is H or has one of the meanings defined for $R_4'$ and
A is branched or unbranched $C_{1-8}$alkylene separating the N and O atoms to which it is attached by 1 to 3 carbon atoms and being optionally substituted by $C_{1-5}$alkoxy or A is linked together with $R_3$ to form 1,3-dioxolane-4-yl-$C_{1-2}$alkylene or 1,3-dioxolane-2-yl-$C_{1-2}$alkylene;

(e) a group

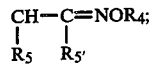

wherein
$R_4$ is as defined above,
$R_5$ and $R_5'$ are independently H or $CH_3$ or $R_5$ together with $R_5$, are $(CH_2)_3$ or $(CH_2)_4$;

(f) allene or $CH_2$—$CH=C=CH_2$; or (g) a group

wherein
$R_6$ is H or $C_{1-3}$alkyl and
B is $N(CH_3)COCH_3$ or a 5-membered saturated lactam ring linked to $CHR_6$ by an N ring atom having adjacent thereto a ring carbonyl function, said lactam ring; (a) optionally containing one additional ring heteroatom selected from the group consisting of O, S and N; (b) optionally containing one additional ring carbonyl function; (c) optionally being substituted by $C_{1-5}$alkyl; and (d) optionally fused to a benzene ring which is optionally substituted by F, Cl or Br, in free base or in acid addition salt form.

19. A herbicidal composition comprising a herbicidally acceptable diluent and a herbicidally effective amount of a compound as defined in claim 1, in free base form or in agriculturally acceptable acid addition salt form.

* * * * *